United States Patent [19]

Murphy et al.

[11] Patent Number: 4,552,758

[45] Date of Patent: Nov. 12, 1985

[54] HUMAN USE OF AVIAN-HUMAN REASSORTANTS AS VACCINES FOR INFLUENZA A VIRUS

[75] Inventors: Brian R. Murphy; Robert M. Chanock, both of Bethesda, Md.; Robert G. Webster, Memphis; Virginia S. Hinshaw, Germantown, both of Tenn.

[73] Assignee: St. Jude Children's Research Hospital, Memphis, Tenn.

[21] Appl. No.: 563,372

[22] Filed: Dec. 20, 1983

[51] Int. Cl.[4] .......................................... A61K 39/145
[52] U.S. Cl. ...................................................... 424/89
[58] Field of Search ........................................ 424/89

[56] References Cited

U.S. PATENT DOCUMENTS

| | | | |
|---|---|---|---|
| 3,992,522 | 11/1976 | Chanock et al. | 424/89 |
| 4,318,903 | 3/1982 | Lobmann et al. | 424/89 |
| 4,338,296 | 9/1982 | Lobmann et al. | 424/89 |
| 4,341,870 | 7/1982 | Wyatt et al. | 435/237 |

OTHER PUBLICATIONS

Murphy et al., Infection and Immunity, 37:1119–1126, Sep. 1982.
Murphy et al., Science, 218:1330–1332, Dec. 24, 1982.
Hinshaw et al., CA. 99#118900r (1983) Virology 1983 128(1): 260–263, Altered Tissue Tropism of Human–Avian Reassortant Influenza Virises.
Kim et al., CA. 87#148423g, (1977) 12v. Akad. Navk. Kaz. SSR, Ser. Biog. 1977, 15(4): 29–35, Effect of Physiochemical Factors on the Enzymic Activity of Influenza Virus From Man and Birds and Their Recombinants.
Pod Chernyaeva CA. 92#211651d (1980).

Primary Examiner—Shep K. Rose
Attorney, Agent, or Firm—John S. Roberts, Jr.

[57] ABSTRACT

A method of producing a live attenuated vaccine useful in humans which comprises producing an influenza A reassortant virus by gene exchange between an avian influenza virus parent and a human influenza virus parent and then excluding the internal genes (that code for non-surface viral proteins) of the human influenza virus parent from the reassortant by temperature selection and excluding the surface antigen genes of the avian influenza A virus parent by antibodies.

2 Claims, No Drawings

HUMAN USE OF AVIAN-HUMAN REASSORTANTS AS VACCINES FOR INFLUENZA A VIRUS

This application is related to a companion application Ser. No. 563,370 filed Dec. 20, 1983 and entitled "Use in an Animal Host and Precursors for Vaccines Utilizing Avian-Human Reassortants to Combat Influenza A Virus."

The subject matter of this application relates to the utilization of avian-human influenza virus reassortants in the prevention of influenza A virus in humans as opposed to the utilization in squirrel monkeys and other animals, as in the companion case above.

STATEMENT OF DEPOSIT

Prior to filing this application and on Oct. 6, 1983, the inventors made a deposit at the American Type Culture Collection, Rockville, Md. This deposit is made under the patent protocol of the ATCC restricting distribution of samples until the issue of a patent when unrestricted use thereof is then directed. Deposit of A/Washington/897/80 X A/Mallard/New York/6750/78 (H3N2) reassortant received ATCC No. VR2072; and deposit of A/California/10/78 X A/Mallard/New York/6750/78 (H1N1) reassortant received ATCC No. VR2073.

MATERIAL INFORMATION DISCLOSURE

U.S. Pat. No. 4,318,903 Löbmann et al. discloses CNCM I-062 strain of influenza virus vaccine prepared by recombination of A/PR/8/34 X A/Alaska/5/77. These two virus strains are human strains differing from the present avian-human influenza virus reassortant.

U.S. Pat. No. 4,338,296 Löbmann et al. discloses CNCM N° I-099 prepared by recombination of influenza A/PR/8/34 X A/California/10/78 and again the recombinant is human/human influenza virus.

U.S. Pat. No. 3,992,522 Chanock et al.

U.S. Pat. No. 4,341,870 Wyatt et al.

Murphy et al., *Infection and Immunity*, 37:1119–1126, September 1982, is a preliminary study prior to the utilization of reassortants wherein avian influenza A virus in squirrel monkeys and hamsters was compared with human influenza A virus.

Murphy et al., Science, 218:1330–1332, Dec. 24, 1982, is a preliminary work showing related work on avian-human reassortants.

DISCLOSURE OF THE INVENTION

This invention relates to the utilization of avian-human influenza virus reassortants in the prevention of influenza A virus infection in humans. It has been described in the companion application that it is possible to produce an influenza A reassortant virus that contains the surface antigen genes of a human influenza A virus and the six internal genes of the avian influenza A virus. These reassortant viruses were attenuated (compared to the human virus) in squirrel monkeys. Thus, the product leads to an attenuation of the virulent human influenza A virus parent. The production of the avian-human reassortant virus is achieved by coinfection of the primary chicken kidney culture by a human and an avian virus at 37° C. and by selection of reassortant progeny at 42° C. It is apparent that at 42° C. there is restriction of replication of human influenza A virus, whereas the avian-human reassortant influenza virus replicates efficiently at this temperature. Generally, the process may be also assisted by the presence of antibodies whose function is to act against the surface antigens of the avian influenza virus parent.

In the development of a human vaccine it is noted that the reassortant virus grows poorly in the human respiratory tract which is consistent with its satisfactory level of attenuation (Table 1).

DOSAGE AND REGIMEN

The dose of the avian-human reassortant virus that infected 50% of seronegative adult patients (volunteers) was $10^{5.9}$ TCID$_{50}$. Thus, at 10 to 100 HID$_{50}$S 80 to 100% of the vaccinees were infected (Table 1).

The avian-human reassortant virus showed acceptable attenuation in susceptible adult patients (volunteers). Of 51 infected vaccinees, only two developed symptoms which were myalgias lasting less than 24 hours. Both illnesses occurred in the group of 19 vaccinees who received the highest dose of virus ($10^{8.0}$ TCID$_{50}$). No respiratory tract symptoms or fever occurred. This level of reactogenicity was significantly less than that observed with wild-type virus which produced illness in 46% of volunteers ($p<0.001$, Chi square test). Consistent with this greatly diminished reactogenicity was a marked reduction in the magnitude and duration of virus shedding. Since avian influenza viruses can cause systemic infections and are enterotropic in their natural hosts, the vaccinees who received $10^{7.0}$ or $10^{8.0}$ TCID$_{50}$ of virus were assessed for systemic spread of virus by testing for viremia or enterotropism by testing for the presence of infectious virus in blood or rectal swabs. Evidence of viremia or enteric replication was not found. Transmission of vaccine virus to six susceptible contacts (three each at $10^{7.0}$ TCID$_{50}$ and $10^{8.0}$ TCID$_{50}$ doses) was also not found.

TABLE 1

RESPONSE OF SERONEGATIVE VOLUNTEERS TO A/WASHINGTON/897/80 (H3N2) AVIAN-HUMAN REASSORTANT OR WILD-TYPE AVIAN

| A/Wash./80 virus administered | Dose of virus (TCID$_{50}$) | Number of Volunteers | % Infected | % Shedding | Virus Shedding (Nasal Wash) | | Serum Antibody Response HAI antibody | |
|---|---|---|---|---|---|---|---|---|
| | | | | | Average* duration (days -SE) | Peak* mean log$_{10}$ titer (TCID$_{50}$/ml -SE) | pre | post |
| Avian-human reassortant | $10^{8.0}$ | 19 | 100 | 47 | 0.5 ± 0.1 | 0.7 ± 0.1 | 2.1 ± 0.2 | 3.8 ± 0.3 |
| | $10^{7.5}$ | 20 | 80 | 10 | 0.1 ± 0.1 | 0.5 ± 0.0 | 1.7 ± 0.2 | 3.8 ± 0.3 |
| | $10^{7.0}$ | 19 | 84 | 11 | 0.3 ± 0.2 | 0.6 ± 0.1 | 1.2 ± 0.1 | 2.6 ± 0.3 |
| | $10^{6.0}$ | 13 | 62 | 8 | 0.2 ± 0.2 | 0.6 ± 0.1 | 2.6 ± 0.3 | 3.5 ± 0.3 |
| | $10^{5.0}$ | 12 | 17 | 17 | 1.5 ± 0.5 | 1.0 ± 0.0 | 2.3 ± 0.3 | 2.5 ± 0.3 |
| Wild type | $10^{6.0}$ | 24 | 96 | 88 | 4.0 ± 0.5 | 3.6 ± 0.4 | 1.8 ± 0.2 | 4.3 ± 0.4 |

| | | Serum Antibody Response | % with rise | % with indicated illness | |
|---|---|---|---|---|---|
| A/Wash./80 | Dose of | % with any | in nasal wash | Febrile, | Upper or |

TABLE 1-continued

RESPONSE OF SERONEGATIVE VOLUNTEERS TO A/WASHINGTON/897/80 (H3N2) AVIAN–HUMAN REASSORTANT OR WILD-TYPE AVIAN

| virus administered | virus (TCID$_{50}$) | Number of Volunteers | NI antibody pre | NI antibody post | rise by HAI, NI, or ELISA | ELISA IgA antibody | systemic, or both | lower respiratory tract | Any |
|---|---|---|---|---|---|---|---|---|---|
| Avian-human reassortant | $10^{8.0}$ | 19 | 2.3 ± 0.4 | 3.6 ± 0.6 | 89 | 74 | 11 | 0 | 11 |
| | $10^{7.5}$ | 20 | 1.8 ± 0.4 | 3.7 ± 0.5 | 75 | 45 | 0 | 0 | 0 |
| | $10^{7.0}$ | 19 | 1.0 ± 0.4 | 2.2 ± 0.4 | 79 | 35 | 0 | 0 | 0 |
| | $10^{6.0}$ | 13 | 1.5 ± 0.5 | 2.6 ± 0.6 | 50 | 25 | 0 | 0 | 0 |
| | $10^{5.0}$ | 12 | 2.0 ± 0.5 | 2.4 ± 0.4 | 8 | 17 | 0 | 0 | 0 |
| Wild type | $10^{6.0}$ | 24 | 0.9 ± 0.3 | 3.2 ± 0.4 | 92 | 93 | 38 | 33 | 46 |

Notes:
Seronegative (HAI titer ≦1.8) volunteers were administered 0.5 ml of virus intranasally.
SE = Standard Error
Virus isolation, antibody response on both signified infection.
Antibody titers are expressed as reciprocal mean log$_2$ titer ± standard error.
Volunteers were considered ill if they developed any of the following syndromes: Fever (>37.8° C.); systemic illness -- the occurrence of myalgia or chills and sweats; upper respiratory tract illness -- rhinitis, pharyngitis, or both observed on two consecutive days; and lower respiratory tract illness -- a persistent cough lasting for at least 2 days. Only volunteers with evidence of infection were included.
*Data from infected volunteers were used for calculations. The lowest detectable quantity of virus shedding was 0.75 TCID$_{50}$/ml.

The live virus vaccine stimulated serum and local antibody. At doses of 10 to 100 HID$_{50}$ approximately 75 to 90% of vaccinees had a serum antibody response and 35 to 74% had a nasal wash antibody response. The mean level of serum HAI antibody response achieved in vaccinees who received 70 to 100 HID$_{50}$S was only slightly less than that found in the recipients of wild-type virus. These findings therefore demonstrate in humans the safety and immunogenicity of a live influenza A reassortant virus exemplified by a virus containing, for example, the surface glycoproteins of the A/Washington/897/80 (H3N2) human virus and the other six RNA segments from the A/Mallard/6750/78 (H2N2) avian influenza virus. These results further indicated that 10 to 100 HID$_{50}$S of the avian-human reassortant (i.e., $10^{7.0}$ to $10^{8.0}$ TCID$_{50}$) given in a 0.5 ml inoculum intranasally by drops is a satisfactory mode of administration. However, any method that administers an effective dosage into the upper respiratory tract is acceptable.

The present invention denotes renewed interest in the development of a live attenuated influenza A virus vaccine since current inactivated influenza virus vaccines do not provide complete protection and do not appear to retain their effectiveness when administered annually. Live attenuated influenza A viruses have been produced by transfer of genes from an attenuated donor virus to new epidemic influenza A viruses. Since resistance to influenza A virus is mediated by the development of an immune response to the hemagglutinin (HA) and neuraminidase (NA) glycoproteins, live, attenuated reassortant vaccine virus strains were selected in which genes for these surface antigens were derived from the epidemic virus, while the non-surface protein ("internal") genes were derived from the attenuated parent. This process of gene exchange is readily achieved with influenza A viruses since they possess a segmented genome consisting of eight negative-stranded RNA segments that code for at least ten proteins. Although genes bearing temperature-sensitive mutations have been transferred to a series of new epidemic wild-type viruses and have rendered such viruses satisfactorily attenuated for man, the genetic instability of the attenuated phenotype represents an insoluble problem.

There is a need for stable attenuated viruses that are unable to escape their attenuation phenotype. Many of the influenza A virus genes that have evolved over a long period in birds differ significantly in nucleotide sequence from corresponding genes of human influenza A viruses. Because of these marked differences some avian influenza viruses would be expected to replicate inefficiently in human cells and thereby be attenuated. Such attenuated avian viruses are also expected to retain their attenuation characteristics after limited replication in man.

This concept was evaluated in animals, including squirrel monkeys, ducks, ferrets, and swine, among others. It was initially evaluated in squirrel monkeys because this primate develops illness similar to humans after experimental infection with influenza A viruses. Ten avian influenza A viruses were evaluated in squirrel monkeys, and a spectrum of replication was observed (Table 2). Some avian influenza viruses replicated almost as well as the human influenza A virus. However, several avian influenza A viruses grow at least 1,000 times less efficiently than human influenza A viruses. Studies were commenced with these latter avian influenza A viruses with the intent of producing avian-human reassortant viruses that are attenuated for man and that could be used as live virus vaccine strains. Restriction of replication of the avian-human reassortant vaccine virus in the primate respiratory tract is effected by naturally occurring avian influenza virus genes rather than by mutant genes selected by limited passage of virus in an unnatural host.

In the prevention of influenza A virus by the reassortant technique, it is noted that here both temperature selection as well as antibodies were utilized, the former to eliminate the non-surface antigen genes of the human influenza virus parent and the latter to eliminate viruses bearing surface antigen genes of the avian parent. In the present case working with influenza A virus, the initial replication temperature for the reassortant product was 37° C. Upon raising the temperature to 42° C., the human virus as well as reassortant viruses containing the human genes that code for non-surface antigens cease to replicate and the utilization of specific antibodies against the surface antigen of the avian influenza parent results in elimination of viruses bearing its surface antigens.

One avian influenza A virus, A/Mallard/New York/6750/78 (H2N2), that was markedly restricted in replication in the trachea of squirrel monkeys, was evaluated as a donor of its non-surface protein genes for attenuation of virulent human influenza A viruses. Avian-human reassortant influenza viruses were produced by mating the avian influenza virus and a virulent human influenza virus in primary chick kidney culture at 37° C. and selecting progeny at 42° C. in the presence of antibodies to the surface antigens of the avian influenza parent virus. The utilization of antibodies as an assistant in the selection process is deemed of easy recognition except in their role as assistants to the temperature selection. As seen in Table 2, 42° C. is restrictive for replication of human influenza A viruses. In matings involving three different virulent human influenza viruses (Table 3), each reassortant virus isolated derived its surface antigen genes from its human influenza virus parent and its "internal" genes from its avian influenza parent virus. Such reassortants will be referred to as "six-gene" reassortants. Like their avian influenza parent virus, each of the avian-human reassortant influenza viruses produced plaques efficiently 42° C. indicating that one or more of the avian influenza genes that code for non-surface proteins specify growth at 42° C. The level of replication of two avian-human reassortant influenza viruses in the lower respiratory tract of the squirrel monkey was compared to that of their parental viruses (Table 4). The two avian-human reassortant influenza viruses were as restricted in growth in the monkey's trachea as their avian influenza parent virus. In each instance the reassortant viruses were shed in lower titer and for a shorter duration than the human influenza virus parent. These findings indicate that restriction of replication of the avian influenza virus is a function of one or more of its "internal" genes. To investigate which of the avian genes was responsible for restricted replication in primates, reassortant viruses were produced that contained human influenza virus surface antigens from the A/Udorn/72 (H3N2) virus and one or more of the internal genes derived from the avian influenza virus parent (Table 5). Avian-human reassortant viruses that contained only an RNA 1, RNA 3, or non-structural (NS) protein RNA segment of avian influenza origin did not exhibit restriction (i.e., they grew to the same level as their human influenza A/Udorn/72 parent). In contrast, avian-human reassortants that contained only the avian nucleoprotein (NP) or matrix (M) protein RNA segment were as restricted in their growth as their avian influenza parent. Avian-human reassortant influenza viruses containing two or more genes derived from their avian influenza parent virus were restricted in replication if they possessed an NP or M gene from the avian parent (Table 6). In addition, the reassortant possessing the RNA 1 and NS genes from the avian parent manifested significant restriction of virus replication in the trachea. This suggests that specific genes, that by themselves do not restrict replication, can act together to effect a reduction in replication. Table 7 shows infection with avian-human influenza reassortant virus induces resistance to challenge with wild type human influenza virus parent.

TABLE 2

EFFICIENCY OF PLAQUE FORMATION OF AVIAN AND HUMAN INFLUENZA A VIRUSES IN TISSUE CULTURE AND THEIR LEVEL OF REPLICATION IN SQUIRREL MONKEYS

| Influenza A Virus* | Antigenic Subtype | Reduction of Plaque Formation+ at 42° C. Compared to 37° C. ($Log_{10}$) | Mean $Log_{10}$ Titer of Virus ($TCID_{50}$/ml) in Tracheal Lavage Fluid |
|---|---|---|---|
| Avian | | | |
| MAL/573/78 | H1N1 | 0.2 | 1.5 |

TABLE 2-continued

EFFICIENCY OF PLAQUE FORMATION OF AVIAN AND HUMAN INFLUENZA A VIRUSES IN TISSUE CULTURE AND THEIR LEVEL OF REPLICATION IN SQUIRREL MONKEYS

| Influenza A Virus* | Antigenic Subtype | Reduction of Plaque Formation+ at 42° C. Compared to 37° C. ($Log_{10}$) | Mean $Log_{10}$ Titer of Virus ($TCID_{50}$/ml) in Tracheal Lavage Fluid |
|---|---|---|---|
| MAL/6750/78 | H2N2 | 0.0 | 2.4 |
| PIN/286/78 | H4N8 | 0.0 | 2.4 |
| PIN/358/79 | H3N6 | 0.0 | 2.8 |
| MAL/827/78 | H8N4 | 0.6 | 2.9 |
| PIN/119/79 | H4N6 | −0.1 | 3.0 |
| TUR/5/79 | H10N7 | −0.1 | 3.1 |
| MAL/88/76 | H3N8 | 0.2 | 4.3 |
| MAL/6874/78 | H3N2 | 0.0 | 4.4 |
| PIN/121/79 | H7N8 | 0.0 | 5.0 |
| Human | | | |
| Udorn/307/72 | H3N2 | >4.6 | 6.5 |
| Wash/897/80 | H3N2 | >5.8 | 5.7 |

+On MDCK or primary chicken kidney cell culture
*Each virus tested in at least four squirrel monkeys

TABLE 3

CONSISTENT TRANSFER OF 6 "INTERNAL" AVIAN[a] INFLUENZA VIRUS GENES TO AVIAN-HUMAN INFLUENZA VIRUS REASSORTANTS WITH H1N1 OR H3N2 SURFACE ANTIGENS

| | Genotype of Avian-Human Influenza Reassortants from Mating of Avian[a] Influenza Virus with Indicated Wild Type Human Influenza Virus[b] | | |
|---|---|---|---|
| Gene | A/Udorn/72(H3N2) | A/Washington/80(H3N2) | A/California/78(H1N1) |
| PB2 | □ | □ | □ |
| PB1 | □ | □ | □ |
| PA | □ | □ | □ |
| HA | ■ | ■ | ■ |
| NA | ■ | ■ | ■ |
| NP | □ | □ | □ |
| M | □ | □ | □ |
| NS | □ | □ | □ |

[a] Avian virus was A/Mallard/New York/6750/78(H2N2)
■ = Gene derived from human wild type virus
□ = Gene derived from avian virus
[b] Progeny from indicated mating selected in the presence of antisera to avian influenza virus surface antigens at 42° C., a temperature restrictive for human influenza virus.

TABLE 4

RESTRICTION OF AVIAN-HUMAN INFLUENZA REASSORTANT VIRUSES IN SQUIRREL MONKEYS

| | | Virus Replication in Trachea | |
|---|---|---|---|
| Influenza A Virus | Number of Monkeys | Average Duration of Virus Shedding (Days) | Mean Peak Titer ($Log_{10}$ $TCID_{50}$/ml) of Tracheal Lavage Fluid |
| Avian | | | |
| A/Mallard/6750/78 | 7 | 2.6[b] | 2.7[b] |
| Reassortant[c] | | | |
| A/Udorn/72 | 6 | 2.0[b] | 2.2[b] |
| A/Washington/80 | 8 | 2.3[b] | 2.7[b] |
| Human Wild Type | | | |
| A/Udorn/72 | 15 | 5.2 | 5.9 |
| A/Washington/80 | 14 | 5.6 | 5.7 |

NOTE:
Monkeys received $10^{7.0}$ $TCID_{50}$ of virus (0.5 ml intratracheally) and were infected in each instance.
[b] Avian virus and reassortants significantly restricted in growth compared to wild type human influenza viruses
[c] Each reassortant contains 6 "internal" avian influenza virus genes.

TABLE 5
EFFECT OF SUBSTITUTION OF A SINGLE AVIAN INFLUENZA VIRUS GENE ON GROWTH OF HUMAN INFLUENZA A VIRUS IN MONKEYS≠

| Influenza Virus△ | Parental Origin of Genes in Avian-Human Influenza Reassortant Viruses | | | | | | | | Virus Replication in Trachea | |
|---|---|---|---|---|---|---|---|---|---|---|
| | RNA1 | RNA2 | RNA3 | HA | NA | NP | M | NS | Average Duration of Virus Shedding (Days) | Mean Peak Titer (Log$_{10}$ TCID$_{50}$/ml) of Tracheal Lavage Fluid |
| Human | □ | □ | □ | □ | □ | □ | □ | □ | 5.3 | 5.1 |
| Avian-Human Reassortant | | | | | | | | | | |
| (a) 6 "internal" avian virus genes | ■ | ■ | ■ | □ | □ | ■ | ■ | ■ | 0.3* | 0.7* |
| (b) Single substitution of an avian virus gene | ■ | □ | □ | □ | □ | □ | □ | □ | 6.0 | 5.2 |
| | □ | □ | ■ | □ | □ | □ | □ | □ | 5.0 | 5.4 |
| | □ | □ | □ | □ | □ | ■ | □ | □ | 0.0* | 0.5* |
| | □ | □ | □ | □ | □ | □ | ■ | □ | 3.3*, 2.0*$^b$ | 2.6*, 1.6*$^b$ |
| | □ | □ | □ | □ | □ | □ | □ | ■ | 5.0 | 4.4 |

≠Avian Virus was A/Mallard/New York/6750/78(H2N2). Human Virus was A/Udorn/307/72(H3N2).
△Each virus tested in at least four squirrel monkeys
*Statistically significant difference from wild type human influenza virus
$^b$Two independently derived reassortants with this gene constellation
□ = Gene derived from human virus
■ = Gene derived from avian virus

TABLE 6
EFFECT OF VARIOUS CONSTELLATIONS OF AVIAN INFLUENZA VIRUS GENES ON GROWTH OF AVIAN-HUMAN INFLUENZA REASSORTANT VIRUSES IN MONKEYS

| Influenza Virus△ | Parental Origin of Genes in Avian-Human Influenza Reassortant Viruses | | | | | | | | Virus Replication in Trachea | |
|---|---|---|---|---|---|---|---|---|---|---|
| | RNA1 | RNA2 | RNA3 | HA | NA | NP | M | NS | Average Duration of Virus Shedding (Days) | Mean Peak Titer (Log$_{10}$ TCID$_{50}$/ml) of Tracheal Lavage Fluid |
| Human | □ | □ | □ | □ | □ | □ | □ | □ | 5.3 | 5.1 |
| Avian-Human Reassortant | | | | | | | | | | |
| (a) 6 "internal" avian virus genes | ■ | ■ | ■ | □ | □ | ■ | ■ | ■ | 0.3* | 0.7* |
| (b) 2 or 3 "internal" avian virus genes | ■ | □ | □ | □ | □ | □ | □ | ■ | 3.5 | 3.2* |
| | □ | □ | ■ | □ | □ | □ | □ | □ | 6.0 | 5.1 |
| | □ | □ | □ | □ | □ | ■ | □ | ■ | 1.0* | 0.9* |
| (c) 5 "internal" avian virus genes | ■ | ■ | □ | □ | □ | ■ | ■ | ■ | 2.0* | 1.7* |
| | ■ | □ | ■ | □ | □ | ■ | ■ | ■ | 0.5* | 0.8* |
| | □ | ■ | ■ | □ | □ | ■ | ■ | ■ | 2.0* | 1.7* |

≠Avian Virus was A/Mallard/New York/6750/78(H2N2). Human Virus was A/Udorn/307/72(H3N2).
△Each virus tested in at least four squirrel monkeys
*Statistically significant difference from wild type human influenza virus
□ = Gene derived from human virus
■ = Gene derived from avian virus

TABLE 7
INFECTION WITH AVIAN-HUMAN INFLUENZA REASSORTANT VIRUS INDUCES RESISTANCE TO CHALLENGE WITH WILD TYPE HUMAN INFLUENZA VIRUS PARENT

| Monkeys Administered 10$^7$ TCID$_{50}$ of Indicated Influenza Virus Intratracheally Four Weeks Pre-Challenge | Number of Monkeys | Virus Replication in Trachea after Intratracheal Administration 10$^{7.0}$ TCID$_{50}$ of Wild Type Human Influenza Virus | |
|---|---|---|---|
| | | Average Duration of Virus Shedding (Days) | Mean Peak Titer (Log$_{10}$ TCID$_{50}$/ml) of Tracheal Lavage Fluid |
| Human Wild Type Virus△ | 6 | 0 | ≦0.5 |
| Avian-Human Reassortant | 5 | 0.4 | 1.0 |
| Avian Virus# | 2 | 6.0 | 3.8 |
| Placebo | 6 | 5.3 | 5.8 |

△Human virus was A/Washington/897/80(H3N2)
Avian virus was A/Mallard/New York/6750/78(H2N2)

We claim:

1. A method of increasing the prevention of influenza A virus in humans which comprises application by intranasal route of an effective amount of 10$^{7.0}$–10$^{8.0}$ TCID$_{50}$ of a reassortant vaccine selected from one member of the group consisting of A/Washington/80 X A/Mallard/New York (H2N2) and A/California/78 X A/Mallard/New York (H2N2).

2. A treatment regimen for preventing influenza A virus in humans which comprises application into the upper respiratory tract an effective dosage of an avian-human reassortant attenuated live virus which comprises administering a dosage of one member of the group consisting of A/Washington/80 X A/Mallard/New York (H2N2) and A/California/78 X A/Mallard/New York (H2N2) in the amount of 10 to 100 $HID_{50}$.

* * * * *